(12) United States Patent
Liang et al.

(10) Patent No.: US 10,233,183 B1
(45) Date of Patent: Mar. 19, 2019

(54) 13-HYDROXYSPARTEINE CINNAMIC ACID DERIVATIVES WITH ANTI-TUMOR ACTIVITIES AND A METHOD OF PREPARING THE SAME

(71) Applicants: Chengyuan Liang, Xi'an (CN); Lei Tian, Xi'an (CN); Yonghong Tang, Xi'an (CN); Minghui Chang, Xi'an (CN); Kaiqi Shi, Xi'an (CN); Xingke Ju, Xi'an (CN); Yuzhi Liu, Xi'an (CN); Lili Wen, Xi'an (CN); Han Li, Xi'an (CN); Xuechuan Wang, Xi'an (CN)

(72) Inventors: Chengyuan Liang, Xi'an (CN); Lei Tian, Xi'an (CN); Yonghong Tang, Xi'an (CN); Minghui Chang, Xi'an (CN); Kaiqi Shi, Xi'an (CN); Xingke Ju, Xi'an (CN); Yuzhi Liu, Xi'an (CN); Lili Wen, Xi'an (CN); Han Li, Xi'an (CN); Xuechuan Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/043,085

(22) Filed: Jul. 23, 2018

(30) Foreign Application Priority Data

Jul. 18, 2018 (CN) .......................... 2018 1 0793138

(51) Int. Cl.
*C07D 471/22* (2006.01)

(52) U.S. Cl.
CPC .................................. *C07D 471/22* (2013.01)

(58) Field of Classification Search
CPC ..................................................... C07D 471/22
USPC ............................................................ 546/63
See application file for complete search history.

(56) References Cited

PUBLICATIONS

Claramunt, R.M. et al.: Conformational analysis of heterocyclic analogues of tetrahydrodibenzocyclooctene: tetrahydrobisbenzimidazoldiazocine and tetrahydrobis pyridodiazocinediium dibromide. Tetrahedron, vol. 54, pp. 9569-9580, 1998.*

* cited by examiner

*Primary Examiner* — Charanjit Aulakh
(74) *Attorney, Agent, or Firm* — SZDC Law P.C.

(57) ABSTRACT

A compound having the following formula I:

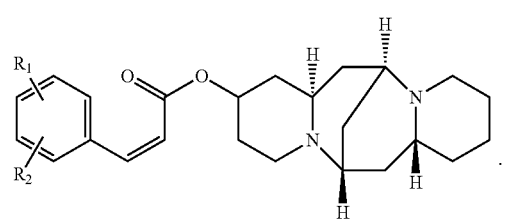

In formula I, $R_1$ and $R_2$ are independently H, alkyl, alkoxy, and halogen. A method of preparing the compound of formula I is also disclosed.

11 Claims, 2 Drawing Sheets

13-HYDROXYSPARTEINE CINNAMIC ACID DERIVATIVES WITH ANTI-TUMOR ACTIVITIES AND A METHOD OF PREPARING THE SAME

The present invention claims priority to Chinese Patent Application No. 201810793138.X, filed on Jul. 18, 2018, which is incorporated by reference for all purposes as if fully set forth herein.

BACKGROUND OF THE INVENTION

Field of the Invention

The present invention relates to the field of pharmaceutical chemistry, and more particularly, to sparteine cinnamic acid derivatives with anti-tumor activities and a method of preparing these derivatives.

Discussion of the Related Art

Tumor is a serious threat to human health. The mechanism of action of anti-tumor drugs and the targets of drugs are different. The development of multidrug resistance in tumor cells often leads to treatment failure. There are needs to develop new safe and effective anti-tumor drugs with few toxic side effects.

Finding safe, effective, and toxic side effects has always been the goal of cancer drug development workers. With the development of medicinal chemistry, the role of compounds with a cinnamic acid structure as a mother core in anti-tumor therapy has attracted widespread attention.

Sparteine (formula II) has a wide range of biological activities, such as anti-arrhythmia, anti-microbial infection, anti-ulcer, and elevated white blood cells. The source of sparteine is widely distributed, and it can be extracted from plants. 13-Hydroxysparteine (formula IIa) is a naturally-occurring sparteine derivative which is isolated from gorse, and it has a structure in which a hydroxy group is added to the 13 position of sparteine.

Cinnamic acid and its partial derivatives are widely distributed in many natural products, such as propolis, vegetables and fruits, and are natural antioxidants. In recent years, studies have shown that cinnamic acid compounds and their derivatives have a wide range of biological activities, such as antioxidant, tyrosinase inhibition, anti-tumor, affecting plant growth and enhancing immunity, in medicine, pesticides, plastics, photosensitive resins, foods. They have a wide range of uses such as additives and flavors and fragrances. The cinnamic acid compounds are natural antioxidants and have strong ability to scavenge free radical DPPH. Studies have shown that the cancerous stage is involved in oxygen free radicals, so cinnamic acid compounds may have some anti-tumor activities.

In the present application, 13-hydroxysparteine is linked with cinnamic acid and its derivatives by an ester bond via a condensation reaction, resulting novel 13-hydroxysparteine cinnamate derivatives. These derivatives have anti-tumor activities and thus important medical application value.

It is an object of the present invention to provide a 13-hydroxysparteine cinnamate derivative having antitumor activity and a method of preparing the same.

SUMMARY OF THE INVENTION

In one embodiment, the present invention provides a compound (a 13-hydroxysparteine cinnamate derivative) having the following formula I:

In formula I, R1 and R2 are independently selected from the group consisting of H, hydroxyl, alkyl, alkoxy, and halogen.

In another embodiment, the compound is selected from the group consisting of:

In one embodiment, the present invention provides a method of preparing the compound. The method includes: reacting a compound of formula III with a compound of formula IIa:

In another embodiment, the compound of formula III is selected from the group consisting of:

In another embodiment, the compound of formula IIa and the compound of formula III react in a molar ratio of 1:1 to 1:1.3, in an organic solvent, in the presence of a catalyst and a condensate, and at 60-100° C. for 4-12 hours.

In another embodiment, the organic solvent is toluene, DMF (dimethylformamide), or acetonitrile.

In another embodiment, the organic solvent is toluene.

In another embodiment, the condensate is DCC (N,N'-dicyclohexylcarbodiimide), EDC (1-ethyl-3-(3-dimethylaminopropyl)carbodiimide), or HOBT (hydroxybenzotriazole).

In another embodiment, the condensate is DCC.

In another embodiment, the catalyst is 4-DMAP (4-dimethylaminopyridine) or triethylamine.

In another embodiment, the molar ratio of the compound of formula IIa and the compound of formula III is 1:1.3.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention. These examples are for illustrative purposes only and do not limit the scope or spirit of the invention.

Example 1

Preparation of (Z)-(6S,7aR,13S,14aR)-tetradecahydro-6,13-methanodipyrido[1,2-a:1',2'-e][1,5]diazocin-2-yl 3-phenylacrylate (Compound A)

A mixture of 25.02 mg (0.10 mmol) 13-hydroxysparteine and 19.25 mg (0.13 mmol) cinnamic acid were dissolved in 50 mL toluene in a reactor. 2.46 mg (0.02 mmol) 4-DMAP and 2.06 mg (0.01 mmol) DCC were added to the mixture, and the mixture was heated at 80° C. for 8 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 29.00 mg compound A as a crystalline compound, a yield of 76.26%.

$^1$H-NMR (400 MHz, DMSO-d$_6$) δ (ppm): 7.60 (2H, d), 7.32-7.40 (4H, m), 6.59 (1H, d), 3.92 (1H, s), 2.72-3.17 (4H, m), 2.64-2.72 (4H, m), 1.76-1.93 (4H, m), 1.48-1.69 (4H, m), 1.45-1.48 (6H, m), 1.18-1.32 (2H, m); $^{13}$C-NMR (75 MHz, DMSO-d6) δ (ppm): 169.0, 139.7, 135.4, 129.0, 128.7, 127.5, 124.5, 65.3, 62.0, 60.8, 56.3, 55.4, 47.9, 39.5, 38.8, 32.1, 28.6, 26.4, 25.0, 23.8; MS (ESI) for (M+H)$^+$: 381.3.

Figure 1:
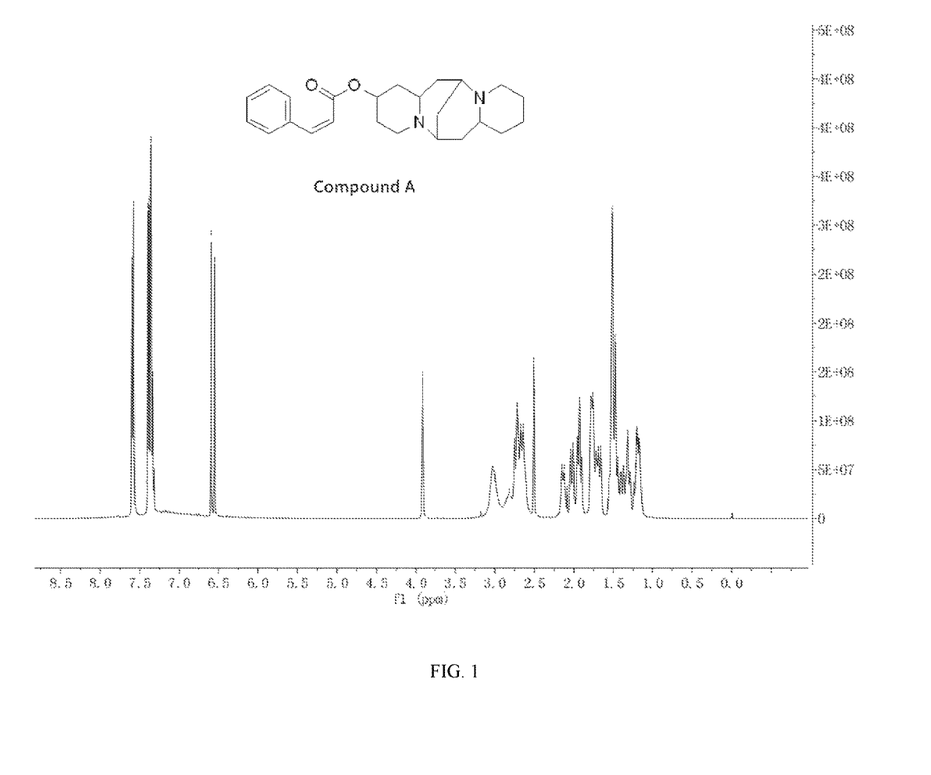
FIG. 1 shows the $^1$H-NMR spectrum of Compound A.
Figure 2:
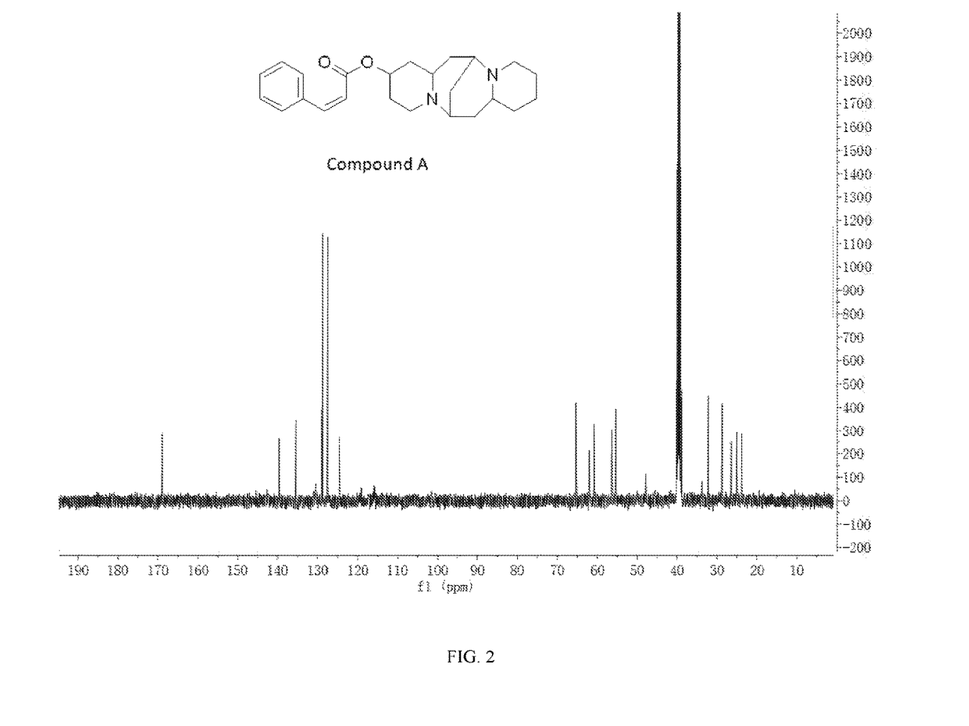
FIG. 2 shows the $^{13}$C-NMR spectrum of Compound A.

The $^1$H-NMR spectrum of Compound A is shown in FIG. 1, and the $^{13}$C-NMR spectrum of Compound A is shown in FIG. 2.

Example 2

Preparation of (Z)-(6S,7aR,13S,14aR)-tetradecahydro-6,13-methanodipyrido[1,2-a:1',2'-e][1,5]diazocin-2-yl 3-(4-hydroxyphenyl)acrylate (Compound B)

A mixture of 25.02 mg (0.10 mmol) 13-hydroxysparteine and 16.40 mg (0.10 mmol) 4-hydroxycinnamic acid were dissolved in 50 mL acetonitrile in a reactor. 2.46 mg (0.02 mmol) 4-DMAP and 2.06 mg (0.01 mmol) DCC were added to the mixture, and the mixture was heated at 80° C. for 12 hours. The solvent (acetonitrile) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 27.94 mg compound B as a crystalline compound, a yield of 70.52%.

$^1$H-NMR (400 MHz, DMSO-d$_6$) δ (ppm): 7.48 (2H, d), 7.37 (1H, d), 6.56 (2H, d), 5.90 (1H, d), 5.28 (1H, s), 5.19 (1H, m), 2.58 (1H, m), 2.32-2.46 (4H, t), 2.13 (3H, m), 1.60-1.80 (4H, m), 1.35-1.52 (6H, t), 1.27-1.51 (6H, m); $^{13}$C-NMR (75 MHz, DMSO-d$_6$) δ (ppm): 167.2, 158.7, 146.3, 131.2, 128.7, 117.3, 116.2, 68.7, 65.4, 62.8, 59.0, 53.4, 47.7, 37.9, 37.2, 35.4, 32.4, 30.4, 27.3, 24.2; MS (ESI) for (M+Na)$^+$: 419.2.

Example 3

Preparation of (Z)-(6S,7aR,13S,14aR)-tetradecahydro-6,13-methanodipyrido[1,2-a:1',2'-e][1,5]diazocin-2-yl 3-(3-hydroxyphenyl)acrylate (Compound C)

A mixture of 25.02 mg (0.10 mmol) 13-hydroxysparteine and 16.40 mg (0.10 mmol) 3-hydroxycinnamic acid were dissolved in 50 mL toluene in a reactor. 2.46 mg (0.02 mmol) 4-DMAP and 2.06 mg (0.01 mmol) DCC were added to the mixture, and the mixture was heated at 80° C. for 4 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 27.13 mg compound C as a crystalline compound, a yield of 68.48%.

$^1$H-NMR (400 MHz, DMSO-$d_6$) δ (ppm): 7.48 (1H, t), 7.40 (1H, d), 7.09 (1H, d), 6.75 (1H, d), 6.62 (1H, s), 5.87 (1H, d), 5.16 (1H, s), 5.13 (1H, m), 2.56 (1H, m), 2.32-2.47 (4H, t), 2.13 (3H, m), 1.59-1.82 (4H, m), 1.34-1.51 (6H, t), 1.26-1.50 (6H, m); $^{13}$C-NMR (75 MHz, DMSO-$d_6$) δ (ppm): 167.5, 158.4, 145.9, 131.6, 128.3, 117.0, 116.2, 68.7, 65.4, 62.9, 59.2, 53.4, 47.2, 37.9, 37.2, 35.3, 32.4, 29.9, 27.2, 24.0; MS (ESI) for (M+H)$^+$: 397.3.

Example 4

Preparation of (Z)-(6S,7aR,13S,14aR)-tetradecahydro-6,13-methanodipyrido[1,2-a:1',2'-e][1,5]diazocin-2-yl 3-(3-hydroxyphenyl)acrylate (Compound D)

A mixture of 25.02 mg (0.10 mmol) 13-hydroxysparteine and 21.32 mg (0.13 mmol) 2-hydroxycinnamic acid were dissolved in 50 mL DMF in a reactor. 2.02 mg (0.02 mmol) triethylamine and 1.35 mg (0.01 mmol) HOBT were added to the mixture, and the mixture was heated at 80° C. for 8 hours. The solvent (DMF) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 24.32 mg compound D as a crystalline compound, a yield of 63.95%.

$^1$H-NMR (400 MHz, DMSO-$d_6$) δ (ppm): 7.61 (1H, d), 7.59 (1H, d), 7.01 (1H, t), 6.82 (1H, t), 6.56 (1H, d), 6.02 (1H, d), 5.19 (1H, s), 5.09 (1H, m), 2.60 (1H, m), 2.46-2.34 (4H, t), 2.15 (3H, m), 1.76-1.80 (2H, q), 1.51-1.59 (2H, t), 1.50-1.57 (6H, t), 1.27-1.36 (6H, m); $^{13}$C-NMR (75 MHz, DMSO-$d_6$) δ (ppm): 167.9, 158.3, 139.8, 130.4, 129.5, 123.1, 122.0, 118.9, 117.3, 68.4, 65.6, 63.0, 59.4, 53.0, 47.1, 38.0, 37.3, 35.4, 32.6, 30.4, 27.0, 24.3; MS (ESI) for (M+Na)$^+$: 419.2.

Example 5

Preparation of (Z)-(6S,7aR,13S,14aR)-tetradecahydro-6,13-methanodipyrido[1,2-a:1',2'-e][1,5]diazocin-2-yl 3-(3,4-dihydroxyphenyl)acrylate (Compound E)

A mixture of 25.02 mg (0.10 mmol) 13-hydroxysparteine and 23.40 mg (0.10 mmol) 3,4-dihydroxycinnamic acid were dissolved in 50 mL DMF in a reactor. 2.46 mg (0.02 mmol) 4-DMAP and 2.06 mg (0.01 mmol) DCC were added to the mixture, and the mixture was heated at 60° C. for 8 hours. The solvent (DMF) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 26.97 mg compound E as a crystalline compound, a yield of 70.93%.

¹H-NMR (400 MHz, DMSO-d₆) δ (ppm): 7.38 (1H, d), 7.12 (1H, s), 7.06 (1H, d), 6.85 (1H, d), 5.89 (1H, d), 5.27 (2H, d), 5.09 (1H, m), 2.60 (1H, m), 2.32-2.45 (4H, t), 2.24 (3H, m), 1.58-1.73 (4H, m), 1.51-1.58 (6H, t), 1.38-1.45 (2H, q), 1.29-1.37 (4H, m); ¹³C-NMR (75 MHz, DMSO-d₆) δ (ppm): 9168.2, 147.7, 147.1, 146.0, 128.6, 124.0, 118.4, 117.1, 116.0, 68.4, 65.6, 63.4, 59.2, 52.9, 47.2, 38.0, 37.3, 35.2, 32.6, 30.3, 27.0, 23.9; MS (ESI) for (M+H)⁺: 413.2.

Example 6

Preparation of (Z)-(6S,7aR,13S,14aR)-tetradeca-hydro-6,13-methanodipyrido[1,2-a:1',2'-e][1,5]di-azocin-2-yl 3-(4-hydroxy-3-methoxyphenyl)acrylate (Compound F)

A mixture of 25.02 mg (0.10 mmol) 13-hydroxysparteine and 25.22 mg (0.13 mmol) 4-hydroxy-3-methoxycinnamic acid were dissolved in 50 mL toluene in a reactor. 2.02 mg (0.02 mmol) triethylamine and 2.06 mg (0.01 mmol) DCC were added to the mixture, and the mixture was heated at 80° C. for 12 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 23.02 mg compound F as a crystalline compound, a yield of 60.55%.

¹H-NMR (400 MHz, DMSO-d₆) δ (ppm): 7.31 (1H, d), 7.03 (1H, s), 7.01 (1H, d), 6.90 (1H, d), 5.85 (1H, d), 5.23 (1H, d), 5.13 (1H, m), 3.73 (1H, s), 2.55 (1H, m), 2.40-2.33 (4H, t), 2.20 (3H, m), 1.49-1.77 (4H, m), 1.43-1.56 (6H, t), 1.30-1.42 (6H, m); ¹³C-NMR (75 MHz, DMSO-d₆) δ (ppm): 167.2, 150.3, 149.3, 146.3, 128.6, 124.2, 117.9, 117.3, 113.5, 68.2, 65.3, 63.4, 59.1, 52.9, 47.6, 37.8, 37.3, 35.2, 32.8, 30.3, 27.0, 23.9; MS (ESI) for (M+Na)⁺: 449.2.

Example 7

Preparation of (Z)-(6S,7aR,13S,14aR)-tetradeca-hydro-6,13-methanodipyrido[1,2-a:1',2'-e][1,5]di-azocin-2-yl 3-(4-hydroxy-3,5-dimethoxyphenyl) acrylate (Compound G)

A mixture of 25.02 mg (0.10 mmol) 13-hydroxysparteine and 22.41 mg (0.10 mmol) 4-hydroxy-3,5-dimethoxycinnamic acid were dissolved in 50 mL acetonitrile in a reactor. 2.46 mg (0.02 mmol) 4-DMAP and 2.06 mg (0.01 mmol) DCC were added to the mixture, and the mixture was heated at 100° C. for 8 hours. The solvent (acetonitrile) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 31.53 mg compound B as a crystalline compound, a yield of 69.11%.

$^1$H-NMR (400 MHz, DMSO-d$_6$) δ (ppm): 7.43 (1H, d), 6.70 (2H, s), 5.92 (1H, d), 5.29 (1H, s), 5.17 (1H, m), 3.77 (6H, s), 2.58 (1H, m), 2.32-2.43 (4H, t), 2.18 (3H, m), 1.63-1.81 (4H, m), 1.51-1.61 (6H, t), 1.22-1.34 (6H, m); $^{13}$C-NMR (75 MHz, DMSO-d$_6$) δ (ppm): 167.5, 149.0, 146.1, 137.6, 127.7, 117.2, 108.2, 68.8, 65.4, 63.1, 59.4, 57.1, 53.4, 47.4, 38.2, 35.7, 33.0, 30.9, 27.5, 24.6; MS (ESI) for (M+H)$^+$: 457.3.

Example 8

Preparation of (Z)-(6S,7aR,13S,14aR)-tetradeca-hydro-6,13-methanodipyrido[1,2-a:1',2'-e][1,5]di-azocin-2-yl 3-(p-tolyl)acrylate (Compound H)

A mixture of 25.02 mg (0.10 mmol) 13-hydroxysparteine and 21.08 mg (0.13 mmol) 4-methylcinnamic acid were dissolved in 50 mL toluene in a reactor. 2.46 mg (0.02 mmol) 4-DMAP and 1.35 mg (0.01 mmol) HOBT were added to the mixture, and the mixture was heated at 100° C. for 4 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 24.24 mg compound H as a crystalline compound, a yield of 61.47%.

$^1$H-NMR (400 MHz, DMSO-d$_6$) δ (ppm): 7.49 (2H, d), 7.39 (1H, d), 7.08 (2H, d), 5.86 (1H, d), 5.12 (1H, m), 2.53 (1H, m), 2.31-2.41 (4H, t), 2.24 (3H, s), 2.13 (3H, m), 1.55-1.77 (4H, m), 1.49-1.53 (6H, t), 1.24-1.38 (6H, m); $^{13}$C-NMR (75 MHz, DMSO-d$_6$) δ (ppm): 167.5, 146.1, 138.6, 133.2, 129.5, 117.2, 68.5, 64.7, 63.0, 59.6, 56.1, 52.9, 47.9, 38.5, 35.3, 33.1, 30.7, 27.2, 23.6, 22.1; MS (ESI) for (M+Na)$^+$: 417.3.

Example 9

Preparation of (Z)-(6S,7aR,13S,14aR)-tetradeca-hydro-6,13-methanodipyrido[1,2-a:1',2'-e][1,5]di-azocin-2-yl 3-(4-hydroxy-3-methylphenyl)acrylate (Compound I)

A mixture of 25.02 mg (0.10 mmol) 13-hydroxysparteine and 23.15 mg (0.13 mmol) 4-hydroxy-3-methylcinnamic acid were dissolved in 50 mL toluene in a reactor. 2.02 mg (0.02 mmol) triethylamine and 1.92 mg (0.01 mmol) EDC were added to the mixture, and the mixture was heated at 60° C. for 8 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 25.98 mg compound I as a crystalline compound, a yield of 63.33%.

$^1$H-NMR (400 MHz, DMSO-d$_6$) δ (ppm): 7.51 (1H, d), 7.40 (1H, d), 7.23 (1H, d), 6.97 (1H, s), 6.01 (1H, d), 5.40 (1H, s), 5.28 (1H, m), 2.67 (1H, m), 2.42-2.51 (4H, t), 2.24 (3H, m), 2.14 (3H, s), 1.67-1.87 (4H, m), 1.52-1.60 (6H, t), 1.36-1.41 (6H, m); $^{13}$C-NMR (75 MHz, DMSO-d$_6$) δ (ppm): 167.0, 153.7, 146.0, 128.2, 125.3, 116.9, 116.3, 68.9, 65.9, 62.9, 59.1, 53.0, 47.3, 38.6, 37.6, 35.6, 33.0, 30.8, 27.4, 24.9, 19.7; MS (ESI) for (M+H)$^+$: 411.6.

Example 10

Preparation of (Z)-(6S,7aR,13S,14aR)-tetradeca-hydro-6,13-methanodipyrido[1,2-a:1',2'-e][1,5]di-azocin-2-yl 3-(m-tolyl)acrylate (Compound J)

A mixture of 25.02 mg (0.10 mmol) 13-hydroxysparteine and 16.21 mg (0.10 mmol) 3-methylcinnamic acid were dissolved in 50 mL acetonitrile in a reactor. 2.46 mg (0.02 mmol) 4-DMAP and 2.06 mg (0.01 mmol) DCC were added to the mixture, and the mixture was heated at 60° C. for 4 hours. The solvent (acetonitrile) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 25.52 mg compound J as a crystalline compound, a yield of 64.72%.

¹H-NMR (400 MHz, DMSO-d₆) δ (ppm): 7.44 (1H, s), 7.36 (1H, d), 7.09 (1H, t), 7.06 (1H, d), 7.04 (1H, s), 5.91 (1H, s), 5.17 (1H, m), 2.58 (1H, m), 2.36-2.46 (4H, m), 2.29 (3H, s), 2.18 (3H, m), 1.60-1.78 (4H, m), 1.35-1.53 (6H, t), 1.29-1.33 (6H, m); ¹³C-NMR (75 MHz, DMSO-d₆) δ (ppm): 167.5, 146.1, 139.3, 136.1, 129.5, 129.2, 127.6, 126.5, 117.2, 68.8, 65.4, 63.2, 63.0, 59.4, 53.4, 47.4, 38.2, 37.8, 35.7, 33.0, 30.9, 27.5, 24.6, 22.7; MS (ESI) for (M+Na)⁺: 417.3.

Example 11

Preparation of (Z)-(6S,7aR,13S,14aR)-tetradecahydro-6,13-methanodipyrido[1,2-a:1',2'-e][1,5]diazocin-2-yl 3-(o-tolyl)acrylate (Compound K)

A mixture of 25.02 mg (0.10 mmol) 13-hydroxysparteine and 21.07 mg (0.10 mmol) 2-methylcinnamic acid were dissolved in 50 mL toluene in a reactor. 2.46 mg (0.02 mmol) 4-DMAP and 2.06 mg (0.01 mmol) DCC were added to the mixture, and the mixture was heated at 100° C. for 12 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 23.02 mg compound K as a crystalline compound, a yield of 65.61%.

¹H-NMR (400 MHz, DMSO-d₆) δ (ppm): 7.66 (1H, s), 7.21 (1H, d), 7.16 (2H, t), 6.91 (1H, d), 6.02 (1H, d), 5.12 (1H, m), 2.53 (1H, m), 2.38-2.41 (4H, t), 2.30 (3H, s), 2.13 (3H, m), 1.55-1.77 (4H, m), 1.49-1.53 (6H, t), 1.24-1.47 (6H, m); ¹³C-NMR (75 MHz, DMSO-d₆) δ (ppm): 168.0, 143.8, 137.7, 137.6, 129.3, 128.9, 127.8, 127.1, 117.7, 69.3, 65.9, 63.7, 63.5, 59.9, 53.9, 47.9, 38.7, 38.3, 36.2, 33.5, 31.4, 28.0, 25.1, 20.7; MS (ESI) for (M+H)⁺: 395.3.

Example 12

Preparation of (Z)-(6S,7aR,13S,14aR)-tetradecahydro-6,13-methanodipyrido[1,2-a:1',2'-e][1,5]diazocin-2-yl 3-(2,4-dimethylphenyl)acrylate (Compound L)

A mixture of 25.02 mg (0.10 mmol) 13-hydroxysparteine and 17.61 mg (0.10 mmol) 2,4-dimethylcinnamic acid were dissolved in 50 mL toluene in a reactor. 2.46 mg (0.02 mmol) 4-DMAP and 2.06 mg (0.01 mmol) DCC were added to the mixture, and the mixture was heated at 80° C. for 4 hours. The solvent (toluene) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 24.43 mg compound L as a crystalline compound, a yield of 59.83%.

¹H-NMR (400 MHz, DMSO-d₆) δ (ppm): 7.61 (1H, d), 7.32 (1H, d), 6.90 (1H, s), 6.84 (1H, d), 5.97 (1H, d), 5.07 (1H, m), 2.58 (1H, m), 2.27-2.36 (4H, t), 2.33 (3H, s), 2.19 (3H, m), 2.08 (3H, m), 1.50-1.72 (4H, m), 1.44-1.48 (6H, t), 1.20-1.25 (6H, m); $^{13}$C-NMR (75 MHz, DMSO-d$_6$) δ (ppm): 168.5, 144.3, 135.8, 135.2, 132.8, 131.8, 127.9, 118.2, 69.8, 66.4, 64.2, 64.0, 54.4, 48.4, 39.2, 38.8, 36.7, 34.0, 31.9, 28.8, 25.6, 23.6, 21.5; MS (ESI) for (M+Na)$^+$: 431.3.

Example 13

Preparation of (Z)-(6S,7aR,13S,14aR)-tetradecahydro-6,13-methanodipyrido[1,2-a:1',2'-e][1,5]diazocin-2-yl 3-(4-chlorophenyl)acrylate (Compound M)

A mixture of 25.02 mg (0.10 mmol) 13-hydroxysparteine and 23.66 mg (0.13 mmol) 4-chlorocinnamic acid were dissolved in 50 mL DMF in a reactor. 2.46 mg (0.02 mmol) 4-DMAP and 1.92 mg (0.01 mmol) EDC were added to the mixture, and the mixture was heated at 80° C. for 8 hours. The solvent (DMF) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 23.98 mg compound M as a crystalline compound, a yield of 57.90%.

$^1$H-NMR (400 MHz, DMSO-$d_6$) δ (ppm): 7.68 (2H, d), 7.49 (1H, s), 7.44 (2H, d), 5.96 (1H, d), 5.22 (1H, m), 2.58 (1H, m), 2.40-2.51 (4H, t), 2.33 (3H, m), 1.65-1.87 (4H, m), 1.42-1.58 (6H, t), 1.34-1.40 (6H, m); $^{13}$C-NMR (75 MHz, DMSO-d$_6$) δ (ppm): 166.5, 144.1, 133.0, 128.2, 127.7, 114.9, 67.8, 63.4, 62.2, 62.0, 56.7, 52.0, 46.1, 35.3, 34.7, 31.4, 29.9, 25.1, 23.1; MS (ESI) for (M+H)$^+$: 415.2.

Example 14

Preparation of (Z)-(6S,7aR,13S,14aR)-tetradecahydro-6,13-methanodipyrido[1,2-a:1',2'-e][1,5]diazocin-2-yl 3-(4-chloro-3-methylphenyl)acrylate (Compound N)

A mixture of 25.02 mg (0.10 mmol) 13-hydroxysparteine and 17.61 mg (0.13 mmol) 4-chloro-3-methylcinnamic acid were dissolved in 50 mL DMF in a reactor. 2.46 mg (0.02 mmol) 4-DMAP and 1.35 mg (0.01 mmol) HOBT were added to the mixture, and the mixture was heated at 80° C. for 8 hours. The solvent (DMF) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 26.15 mg compound N as a crystalline compound, a yield of 61.07%.

$^1$H-NMR (400 MHz, DMSO-d$_6$) δ (ppm): 7.49 (2H, d), 7.49 (1H, s), 7.21 (1H, d), 6.95 (1H, s) 5.91 (1H, d), 5.17 (1H, m), 2.46 (1H, m), 2.46-2.50 (4H, t), 2.36 (3H, d), 2.12 (3H, m), 1.60-1.83 (4H, m), 1.43-1.55 (6H, t), 1.31-1.42 (6H, m); $^{13}$C-NMR (75 MHz, DMSO-d$_6$) δ (ppm): 165.9, 145.1, 133.8, 132.1, 128.2, 126.9, 125.4, 115.4, 66.9, 64.3, 62.0, 61.3, 58.1, 51.7, 45.8, 36.0, 34.4, 32.0, 29.7, 24.1, 23.5, 20.3; MS (ESI) for (M+Na)$^+$: 451.2.

Example 15

Preparation of (Z)-(6S,7aR,13S,14aR)-tetradecahydro-6,13-methanodipyrido[1,2-a:1',2'-e][1,5]diazocin-2-yl 3-(4-bromophenyl)acrylate (Compound O)

A mixture of 25.02 mg (0.10 mmol) 13-hydroxysparteine and 29.38 mg (0.13 mmol) 4-bromocinnamic acid were dissolved in 50 mL acetonitrile in a reactor. 2.02 mg (0.02 mmol) triethylamine and 2.06 mg (0.01 mmol) DCC were added to the mixture, and the mixture was heated at 80° C. for 8 hours. The solvent (acetonitrile) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 30.34 mg compound O as a crystalline compound, a yield of 66.22%.

$^1$H-NMR (400 MHz, DMSO-d$_6$) δ (ppm): 7.68 (2H, d), 7.46 (2H, d), 7.40 (1H, d), 5.89 (1H, d), 5.21 (1H, m), 2.61 (1H, m), 2.40-2.54 (4H, t), 2.33 (3H, m), 1.59-1.81 (4H, m), 1.57-1.65 (6H, m), 1.31-1.48 (6H, m); $^{13}$C-NMR (75 MHz, DMSO-d$_6$) δ (ppm): 165.6, 145.1, 132.7, 127.5, 120.7, 115.1, 67.8, 63.4, 62.0, 61.3, 57.2, 52.3, 45.6, 37.2, 35.4, 34.1, 31.7, 28.8, 26.5, 23.2; MS (ESI) for (M+H)$^+$: 459.2.

Example 16

Preparation of (Z)-(6S,7aR,13S,14aR)-tetradecahydro-6,13-methanodipyrido[1,2-a:1',2'-e][1,5]diazocin-2-yl 3-(4-bromo-3-methoxyphenyl)acrylate (Compound P)

A mixture of 25.02 mg (0.10 mmol) 13-hydroxysparteine and 33.28 mg (0.13 mmol) 4-bromo-3-methoxycinnamic acid were dissolved in 50 mL acetonitrile in a reactor. 2.02 mg (0.02 mmol) triethylamine and 2.06 mg (0.01 mmol) DCC were added to the mixture, and the mixture was heated at 60° C. for 12 hours. The solvent (acetonitrile) in the mixture was removed under reduced pressure. Ethyl acetate was added to the mixture, and mixture was washed with water, sodium bicarbonate solution, and sodium chloride solution. The solvent (ethyl acetate) in the mixture was removed under reduced pressure. The mixture was then cooled down and filtered to give 33.54 mg compound P as a crystalline compound, a yield of 68.70%.

$^1$H-NMR (400 MHz, DMSO-d$_6$) δ (ppm): 7.39 (1H, s), 7.30 (1H, d), 7.09 (1H, d), 6.82 (1H, s), 5.88 (1H, d), 5.13 (1H, m), 3.81 (3H, s), 2.46 (1H, m), 2.28-2.49 (4H, m), 2.26 (3H, m), 1.61-1.77 (4H, m), 1.42-1.59 (6H, m), 1.27-1.40 (6H, m); $^{13}$C-NMR (75 MHz, DMSO-d$_6$) δ (ppm): 164.6, 155.3, 143.8, 133.7, 132.4, 119.2, 115.4, 112.5, 110.6, 67.0, 64.4, 62.1, 57.6, 54.7, 50.6, 45.9, 36.4, 33.3, 31.0, 28.4, 25.1, 22.4; MS (ESI) for (M+Na)$^+$: 511.16.

Example 17

The compounds of the present invention were subjected to tumor cell proliferation inhibition test, and conventional MTT method was used.

Cell lines used: non-small cell lung cancer cells (H1975), human hepatoma cells (HepG2), human glioma cells (U251), human gastric adenocarcinoma cells (AGS), human breast cancer cells (1590). The culture medium was DMEM+15% NBS+double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Antitumor cytarabine (Ara-C) was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% CO$_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and IC$_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$ (unit: μmol/L)

| | $IC_{50}$ (μmol/L) | | | | |
|---|---|---|---|---|---|
| Comp | H1975 | HepG2 | U251 | AGS | 1590 |
| A | 16.89 ± 1.36 | 36.55 ± 3.01 | >100 | 20.34 ± 1.12 | 32.01 ± 1.69 |
| B | >100 | 53.69 ± 0.34 | 74.98 ± 0.49 | >100 | >100 |
| C | 23.69 ± 2.37 | 73.55 ± 0.49 | 5.49 ± 1.98 | 26.34 ± 1.48 | 43.21 ± 0.95 |
| D | 9.48 ± 1.48 | 11.84 ± 2.48 | 63.14 ± 0.75 | 51.84 ± 0.31 | 33.67 ± 1.11 |
| E | 43.15 ± 1.24 | >100 | 42.16 ± 0.88 | >100 | 36.21 ± 1.98 |
| F | >100 | >100 | >100 | >100 | 88.64 ± 2.12 |
| G | 55.48 ± 0.48 | >100 | 36.98 ± 1.24 | 59.44 ± 0.97 | >100 |
| H | 29.89 ± 1.59 | 51.14 ± 1.44 | 75.44 ± 0.897 | 35.67 ± 2.58 | >100 |
| I | >100 | 58.66 ± 1.78 | 66.89 ± 1.84 | 32.59 ± 0.29 | >100 |
| J | 64.98 ± 1.89 | 88.46 ± 1.26 | 74.62 ± 2.94 | >100 | 65.43 ± 0.47 |
| K | 89.63 ± 1.34 | >100 | >100 | 69.81 ± .060 | >100 |
| M | >100 | 26.84 ± 1.24 | 45.88 ± 1.82 | 55.54 ± .044 | 10.59 ± 1.33 |
| Ara-C | 19.17 ± 0.39 | 20.64 ± 0.54 | 39.16 ± 0.54 | >100 | 76.31 ± 2.48 |

The results show that these compounds have good antitumor activities. Specifically, Compounds A, C, D, E, G, H, I and M show good in vitro antitumor activities in different cell lines. The above experimental results indicate that the compounds (sparteine cinnamic acid derivatives) of the present invention have good antitumor activities and can be used for the study of antitumor agents.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound having the following formula I:

I wherein $R_1$ and $R_2$ are independently selected from the group consisting of H, hydroxyl, alkyl, alkoxy, and halogen.

2. The compound of claim 1, wherein the compound is selected from the group consisting of:

A

-continued

B

C

D and

3. A method of preparing the compound of claim 1 comprising:

reacting a compound of formula III with a compound of formula IIa:

-continued

IIa

I

4. The method of claim 3, wherein the compound of formula III is selected from the group consisting of:

-continued

5. The method of claim 3, wherein the compound of formula IIa and the compound of formula III react in a molar ratio of 1:1 to 1:1.3, in an organic solvent, in the presence of a catalyst and a condensate, and at 60-100° C. for 4-12 hours.

6. The method of claim 5, wherein the organic solvent is toluene, DMF, or acetonitrile.

7. The method of claim 6, wherein the organic solvent is toluene.

8. The method of claim 5, wherein the condensate is DCC, EDC, or HOBT.

9. The method of claim 8, wherein the condensate is DCC.

10. The method of claim 5, wherein the catalyst is 4-DMAP or triethylamine.

11. The method of claim 5, wherein the molar ratio of the compound of formula IIa and the compound of formula III is 1:1.3.

* * * * *